United States Patent [19]

Hsiao

[11] Patent Number: 4,708,867

[45] Date of Patent: Nov. 24, 1987

[54] MINIPELLETS

[75] Inventor: Charles H. Hsiao, Cooper City, Fla.

[73] Assignee: Key Pharmaceuticals, Inc., Miami, Fla.

[21] Appl. No.: 587,536

[22] Filed: Mar. 8, 1984

Related U.S. Application Data

[63] Continuation-in-part of Ser. No. 564,852, Dec. 19, 1983, abandoned.

[51] Int. Cl.⁴ .......................... A61K 9/28; A61K 9/32; A61K 9/58
[52] U.S. Cl. ...................................... 424/80; 424/458; 424/470; 424/474; 424/482; 424/489
[58] Field of Search ..................... 424/81, 33, 80, 458, 424/470, 474, 482, 489

[56] References Cited

U.S. PATENT DOCUMENTS

| | | | |
|---|---|---|---|
| 3,775,537 | 11/1973 | Lehmann et al. | 424/33 |
| 3,959,540 | 5/1976 | Leiberich et al. | 424/33 |
| 4,101,651 | 7/1978 | Kobayashi et al. | 424/81 |
| 4,150,110 | 4/1979 | Yoshida et al. | 424/81 |
| 4,341,759 | 7/1982 | Bogentoft et al. | 424/33 |

OTHER PUBLICATIONS

Eudragit E Data Sheet (Info E-3/e), Eudragit E Application in the Production of Pharmaceutical Preparations.

Primary Examiner—Shep K. Rose
Attorney, Agent, or Firm—Anita W. Magatti; James R. Nelson; Stephen I. Miller

[57] ABSTRACT

A minipellet dosage form of prednisone or prednisolone, resistant to attack by saliva but readily dissolvable in gastric juice, which comprises a mixture of prednisone or prednisolone and polyvinylpyrrolidone coated onto a nonpareil seed, and further coated with a layer of dimethylaminoethyl and methyl methacrylate copolymer.

5 Claims, No Drawings

MINIPELLETS

This application is a continuation-in-part of my copending application Ser. No. 564,852, filed on Dec. 19, 1983 now abandoned.

BACKGROUND OF THE INVENTION

The present invention relates to an improved dosage form for prednisone or prednisolone. More particularly, it relates to minipellets coated to mask the unpleasant taste of those compounds.

Prednisone, $17\alpha$, 21-dihydroxypregna-1,4-diene-3,11,20-trione, also named 1,4-pregnadiene-$17\alpha$, 21-diol-3,11,20-trione, and prednisolone, also named of $11\beta,17,21$-trihydroxypregna-1,4-diene-3,20-dione, are well known adrenocortical steroids. They are available as 1 to 50 mg tablets; and the usual oral dose is from 5 to 50 mg per day. Both are described as having a very bitter taste, unpleasant to adults and particularly unpleasant to children. While it is possible to administer prednisone or prednisolone in a conventional gelatin capsule, children are often unwilling to swallow capsules and older adults may be unable to swallow them. Accordingly, it would be desirable to provide these medicaments in minipellet form coated to mask their unpleasant taste. However, the United States Pharmacopeia requires that dosage forms containing prednisone or prednisolone be almost completely dissolved within 30 minutes after administration; prednisone or prednisolone coated with the usual tablet coatings would not meet that test.

The present invention provides a prednisone or prednisolone minipellet which, when ingested, does not exhibit a bitter taste in the mouth but is rapidly dissolved in the stomach.

In its broadest aspect, the present invention is a minipellet comprising prednisone or prednisolone admixed with polyvinylpyrrolidone coated on a nonpareil seed, and further coated with a copolymer of dimethylaminoethyl and methyl methacrylate.

More specifically, the present invention is a minipellet dosage form of prednisone or prednisolene resistant to attack by saliva but readily dissolvable in gastric juice which comprises a mixture of prednisone or prednisolone and polyvinylpyrrolidone coated onto a nonpareil seed, and further coated with a copolymer of dimethylaminoethyl and methyl methacrylate.

In another aspect, the invention contemplates a unit dosage of said minipellets in a readily opened container such as an unsealed capsule.

The copolymer utilized in practicing the present invention is a cationic copolymer available under the trade name Eudragit E 100. That copolymer forms a coating resistant to saliva and effectively masks any unpleasant taste in the mouth, but becomes water soluble in the stomach very quickly by forming a salt with the hydrochloric acid present in the gastric juice.

In preparing minipellets according to the present invention, micronized prednisone or prednisolone is suspended in a solution of polyvinylpyrrolidone dissolved in a suitable organic solvent, preferably isopropyl alcohol. The suspension and/or solution is coated onto nonpareil sugar seeds, preferably 30-60 mesh in size, using conventional equipment. The minipellets coated with prednisone or prednisolone and polyvinylpyrrolidone are further coated with an organic solvent solution of dimethylaminoethyl and methyl methacrylate. While not required, the addition of separation substances, such as talc, magnesium stearate and pigments, decreases the tendency of the polymer to agglutinate and produces a more uniform surface on the resultant minipellet. After drying, an appropriate number of minipellets are placed in a capsule to provide the desired dosage. The capsule should be readily openable by an elderly person to avoid unintentional spilling and loss of minipellets. Typically, the capsule is opened just before use and the minipellets sprinkled onto a food which is then eaten as part of a meal or snack.

My invention is further illustrated by means of the following non-limiting example.

500 gm nonpareil sugar seeds, mesh size of between 35-40, were placed in a preheated air suspension coating column (4"-6" Wurster column manufactured by Glatt, West Germany). The seeds were coated with 80 gm of prednisone suspended in a solution containing 40 gm of polyvinylpyrrolidone in 800 ml of isopropyl alcohol and dried. The dried pellets were further coated with a solution containing 288 gm of dimethylaminoethyl and methyl methacrylate copolymer (Eudragit E 100) in 1600 ml of acetone and 1600 ml of isopropyl alcohol. After the polymer solution/suspension had been applied, the resultant minipellets were dried and hand-filled into No. 3 size clear gelatin capsules. Each capsule contained about 200 minipellets or 10 mg of prednisone.

Minipellets as prepared in the previous example were suspended in various food preparations which were given to a four-person panel for taste testing. The results are summarized in the table which follows:

TABLE

| Time in Minutes | Beef | | Chicken | | Pudding | | | Vegetable | | Apple | | | Pear | | |
|---|---|---|---|---|---|---|---|---|---|---|---|---|---|---|---|
| | 5 | 10 | 5 | 10 | 5 | 10 | 26 | 5 | 10 | 2 | 4 | 5 | 2 | 4 | 5 |
| I | O | T | O | O | O | O | O | O | O | O | O | T | O | O | T |
| II | O | O | O | O | O | O | O | O | O | O | O | T | O | O | T |
| III | O | O | O | O | O | O | O | O | O | O | O | T | O | O | T |
| IV | O | O | O | O | O | O | O | O | O | O | O | T | O | O | T |

O indicates no taste detected
T indicates taste detected

Almost no taste was detected in non-acid food preparations (beef, chicken, pudding and vegetables). Taste was detected in acid fruit products (apple and pear) after 5 minutes.

Minipellets produced in accordance with the procedure of Example I, when tasted in the simulated gastric juice test procedure described in U.S.P. XI, dissolved within 30 minutes.

I claim:

1. A minipellet dosage form of prednisone or prednisolone, resistant to attack by saliva but readily dissolvable in gastric juice, consisting essentially of a nonpareil seed having coated thereon a first layer comprising a mixture of a prednisone or prednisolone and polyvinylpyrrolidone and a second layer of dimethylaminoethyl and methyl methacrylate copolymer, the minipellet being substantially dissolved in 30 minutes on contact with gastric juice.

2. A dosage form according to claim 1 wherein the minipellets are approximately 25–35 mesh in size.

3. A dosage form according to claim 1 wherein a unit dosage of minipellets is contained in an unsealed capsule.

4. A dosage form according to claim 1 which contains prednisone.

5. A dosage form according to claim 1 which contains prednisolone.

* * * * *